(12) United States Patent
Fanto' et al.

(10) Patent No.: US 7,169,808 B2
(45) Date of Patent: Jan. 30, 2007

(54) COMPOUNDS USEFUL FOR THE PREPARATION OF MEDICAMENTS WITH PHOSPHODIESTERASE IV INHIBITORY ACTIVITY

(75) Inventors: Nicola Fanto', Pomezia (IT); Maria Ornella Tinti, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 150 days.

(21) Appl. No.: 10/311,756

(22) PCT Filed: Jun. 15, 2001

(86) PCT No.: PCT/IT01/00312

§ 371 (c)(1),
(2), (4) Date: Dec. 19, 2002

(87) PCT Pub. No.: WO02/00593

PCT Pub. Date: Jan. 3, 2002

(65) Prior Publication Data

US 2003/0195257 A1    Oct. 16, 2003

(30) Foreign Application Priority Data

Jun. 23, 2000    (IT) .................. RM2000A0341

(51) Int. Cl.
*A61K 31/215*    (2006.01)
*C07C 69/76*    (2006.01)
*C07C 259/04*    (2006.01)

(52) U.S. Cl. .................... 514/507; 560/61; 562/621
(58) Field of Classification Search ............ 560/61; 562/621; 514/507
See application file for complete search history.

(56) References Cited

U.S. PATENT DOCUMENTS

| | | | | |
|---|---|---|---|---|
| 3,714,356 | A * | 1/1973 | Burrous et al. | 514/198 |
| 4,335,054 | A * | 6/1982 | Blaser et al. | 558/377 |
| 4,820,828 | A * | 4/1989 | Demers et al. | 549/362 |
| 4,971,959 | A * | 11/1990 | Hawkins | 514/150 |
| 6,235,739 | B1 * | 5/2001 | Ina et al. | 514/247 |

FOREIGN PATENT DOCUMENTS

| | | |
|---|---|---|
| EP | 0 511 865 | 11/1992 |
| EP | 0 933 366 | 8/1999 |
| WO | 92 00968 | 1/1992 |
| WO | 92 19594 | 11/1992 |
| WO | 95 08534 | 3/1995 |
| WO | 97 05098 | 2/1997 |
| WO | 97 05105 | 2/1997 |
| WO | 99 05143 | 2/1999 |
| WO | 99 15494 | 4/1999 |
| WO | WO 99/15494 | * 4/1999 |
| WO | 99 30709 | 6/1999 |
| WO | WO 00/35915 | * 6/2000 |
| WO | 01 32649 | 5/2001 |

OTHER PUBLICATIONS

Budavari, The Merck Index, 12th Edition, p. 267.*
Yamamoto et al, Chemical & Pharmaceutical Bulletin, 1982, vol. 30 (10), pp. 3601-3616.*
Rao et al, Current Science, 1969, 38(4), pp. 90-91.*
Search Report and International Preliminary Examination Report for PCT IT 01/312.*
CA 116:202019 abstract for Farkas et al, Journal of Coordination Chemistry, 24 (4) pp. 325-332 (1991).*
Nicholson et al., Pulmonary Pharmacology, vol. 7, No. 1, pp. 1-17 (1994).*
Banner et al., European Respiratory Journal, vol. 8, pp. 996-1000 (1995).*
Badger et al, "Beneficial effects of the phosphodiesterase inhibitors BRL 61063, pentoxifyline, and rolipram in a murine model of endotoxin shock", Circ Shock, Dec. 1994; 44(4):188-95.
S. Budavari (Ed): "The Merk Index (12th edition)", Merck & Co, Whitehouse Station, NJ XP002184331 p. 267, paragraph 1673-p. 268 (1996).
S. Budavari (Ed): "The Merk Index (12th edition)", Merck & Co, Whitehouse Station, NJ XP002184332 p. 933, paragraph 5490-p. 934 (1996).
S. Budavari (Ed): "The Merk Index (12th edition)", Merck & Co, Whitehouse Station, NJ XP002184333 p. 1034, paragraph 6133 (1996).
Buu-Hoi, N. P. et el: "Synthesis and pharmacological properties of substituted cinnamohydroxamic acids" J. Med. Chem. (1970), 13(2), 211-13, 1970, XP002184329 p. 212; examples 9-11, 14-16, 19-21, 28, 29, 31-33; table 1.
Hebel, David et al: "Selective monoflurination of biologically interesting compounds using acetyl hypolluorite" Bull, Soc. Chim. Fr. (1986), (6), 861-3, 1986, XP002184330, p. 861; figure 5, p. 863, paragraph 2.

* cited by examiner

*Primary Examiner*—Porfirio Nazario-Gonzalez
(74) *Attorney, Agent, or Firm*—Nixon & Vanderhye P.C.

(57) ABSTRACT

Formula (I) compounds are described, where the groups are defined in the description, as well as processes for their preparation and their use as medicaments, particularly as selective phosphodiesterase IV inhibitors.

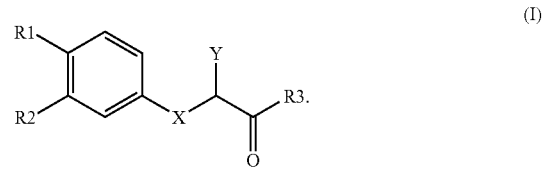

(I)

13 Claims, No Drawings

COMPOUNDS USEFUL FOR THE PREPARATION OF MEDICAMENTS WITH PHOSPHODIESTERASE IV INHIBITORY ACTIVITY

This application is the U.S. National Phase of International Application PCT/IT01/00312 filed 15 Jun. 2001, which designated the U.S.

The invention described herein relates to compounds for use as medicaments, to processes for their preparation, to pharmaceutical compositions containing them and to their use for the preparation of medicaments, and more particularly for medicaments useful as selective phosphodiesterase IV inhibitors.

The phosphodiesterases are a large family of enzymes which act on different substrates over an extensive area of metabolic regulation. For a review of the subject see C. David et al. TiPS—January 1991 (vol. 12); 19–27.

It is well known that there are at least 5 distinct families of phosphodiesterase isoenzymes (briefly PDE I-V) (see Beavo & Houslay, Isoenzymes of Cyclic Nucleotide Phosphodiesterase. Chichester: Wiley & Sons—1990).

There is therefore still a need for selective phosphodiesterase inhibitors.

In particular, the invention described herein tackles the problem of supplying selective inhibitors of phosphodiesterase IV (briefly, also referred to as PDE IV).

Phosphodiesterase IV inhibitors are also known as useful agents in the treatment of respiratory tract diseases, particularly as anti-inflammatory agents and bronchodilators.

Among the most studied PDE IV inhibitors, we mention here rolipram (Reeves et al. Biochem J., 241, 535–541 (1987), U.S. Pat. No. 4,193,926 and U.S. Pat. No. 5,059,612) and denbufylline (Nicholson et al. Br. J. of Pharmacol., 97, 889–897 (1989)), as useful agents for the treatment of asthma thanks to their bronchodilatory properties.

2-aminotetralines are described, for example, in Italian patent IT 1232359, as antihypertensive agents; in U.S. Pat. No. 5,637,614, as immunomodulators; and in U.S. Pat. No. 5,591,777, WO98/33762, WO99/15494, as agents useful for the treatment and prevention of septic shock.

WO 9704775 describes substituted dihydropyridopyrimidines as selective inhibitors of PDE IV.

It has now been found that 6,7-disubstituted 2-aminotetralines are selective inhibitors of phosphodiesterase IV.

Compounds of general formula (I) are the subject matter of the invention described herein:

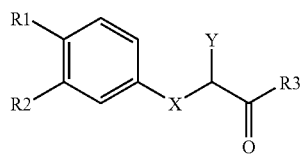

where:

$R_1$ and $R_2$, which may be the same or different, are halogen, hydroxy, straight or branched $C_1$–$C_4$ alkoxy, $C_5$–$C_6$ cycloalkoxy;

X is —(CH$_2$)$_n$—, —CO—(CH$_2$)$_n$—, where n is 1 or 2, or X is —CH=;

$R_3$ is —OH, —NHOH, straight or branched $C_1$–$C_4$ alkoxy;

Y is H, —(CH$_2$)$_n$COR$_4$, —COR$_4$, —NHR$_5$, where $R_4$ is —OH, —NHOH, straight or branched $C_1$–$C_4$ alkoxy, $R_5$ is H, $C_1$–$C_4$ alkanoyl optionally substituted by halogens;

n is an integer between 1 and 4, extremes included;

their enantiomers, diastereoisomers and mixtures of the same, and their pharmaceutically acceptable salts.

A first preferred group of formula (I) compounds are those in which $R_1$ is halogen and $R_2$ alkoxy or cycloalkoxy; in particular, within this group, the preference goes to compounds in which $R_2$ is cyclopentyloxy.

A second preferred group of formula (I) compounds are those in which $R_3$ is —NHOH.

A third preferred group of formula (I) compounds are those in which X is —CH=.

A fourth preferred group of formula (I) compounds are those in which $R_3$ is —OH.

A fifth preferred group of formula (I) compounds are those in which Y is —(CH$_2$)$_n$COR$_4$, where n is 1 and $R_4$ is —NHOH.

A sixth preferred group of formula (I) compounds are those in which Y is —(CH$_2$)$_n$COR$_4$, where n is 2 and $R_4$ is —OH.

A seventh preferred group of formula (I) compounds are those in which Y is —(CH$_2$)$_n$COR$_4$, where n is 1 and $R_4$ is straight or branched $C_1$–$C_4$ alkoxy, in particular —CH$_3$.

The following compounds are preferred:

(S)-2-(N-trifluoroacetyl)amino-4-(3-fluoro-4-methoxyphenyl)-butane-hydroxamic acid (ST1471);

(S)-2-amino-4-(3-fluoro-4-methoxyphenyl)-butane-hydroxamic acid (ST1496);

(3E)-3-methoxycarbonyl-4-(3-cyclopentoxy-4-methoxyphenyl)-3-butenoic acid (ST1503);

(R,S)-3-methoxycarbonyl-4-(3-cyclopentoxy-4-methoxyphenyl)-butanoic acid (ST1504);

4-oxo-4-(3-cyclopentyloxy-4-methoxyphenyl)-butanoic acid (ST1689);

methyl (2E)-3-[3-(cyclopentyloxy)-4-methoxyphenyl]-2-[2-(hydroxyamino)-2-oxoethyl]-2-propenoate (ST 1701);

4-(3-fluoro-4-methoxyphenyl)-4-oxo-2-[(trifluoroacetyl)-amino]-butanoic acid (ST1738);

(2S)-4-(3-fluoro-4-methoxyphenyl)-4-oxo-2-[(trifluoroacetyl)amino]butanoic acid (ST1739);

4-(3-fluoro-4-methoxyphenyl)-2-[(trifluoroacetyl) amino]-butanoic acid (ST1741);

(R,S)-3-methoxycarbonyl-4-(3-cyclopentyloxy-methoxyphenyl)butane-hydroxamic acid (ST1505);

methyl (3E)-3-methoxycarbonyl-4-(3-cyclopentoxy-4-methoxyphenyl)-3-butenoate (ST 1945);

(4E)-5-[3-(ciclopentyloxy)-4-methoxyphenyl]-4-(methoxycarbonyl)-4-pentenoic acid (ST 1977).

The compounds according to the invention described herein can be prepared according to known methods.

In particular, in the case of the formula (I) compounds in which $R_3$ is —NHOH, the groups $R_1$ and $R_2$ are halogen and hydroxy or alkoxy or cycloalkoxy, Y is —NHR$_4$, and X is —(CH$_2$)$_n$—, these are preferably prepared with the process described, entirely by way of an example, for compounds ST1471 and ST1496, which involves a series of reactions according to the reaction diagram indicated here below.

Diagram 1

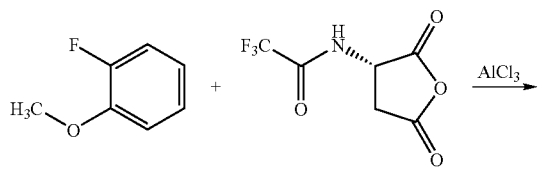

1

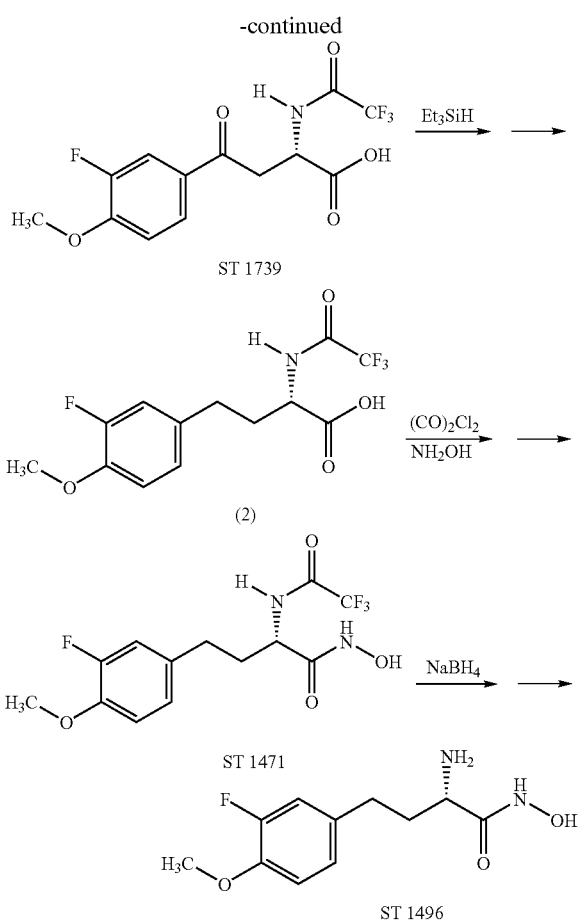

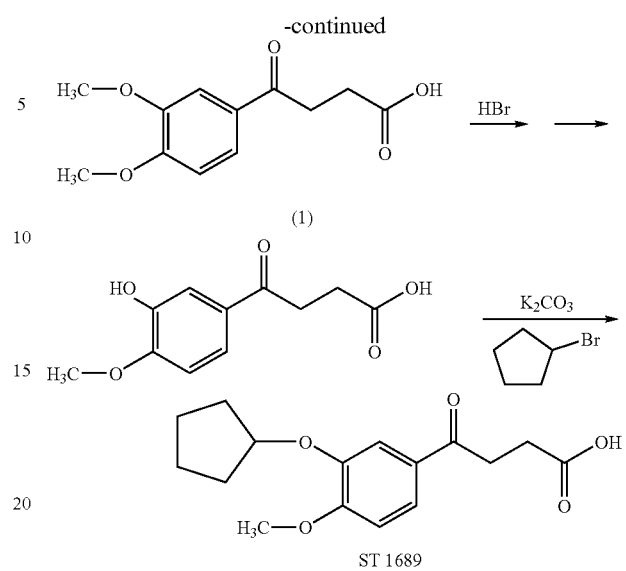

It is understood that the expert in the field is capable of preparing all the formula (I) compounds, in which $R_1$ and $R_2$ are as specified in the general description, selecting the appropriate starting compounds. By way of an example, an appropriate starting compound will be selected from the group consisting of benzene 1,2, substituted with the groups $R_1$ and $R_2$ indicated above, such as 2,3-dimethoxybenzene, 2,3-diethoxybenzene, 2,3-dipropoxybenzene, 2,3-dibutoxybenzene, and the branched isomeric analogues, or 2,3-dicyclopentyloxybenzene, 2,3-dicyclohexyloxybenzene. Starting compounds carrying different $R_1$ and $R_2$ groups are also envisaged. These compounds are commercially available or can be prepared with known methods in the literature.

In particular, in the case of formula (I) compounds in which $R_3$ is —OH, the groups $R_1$ and $R_2$ are halogen and hydroxy or alkoxy or cycloalkoxy, Y is —$NHR_4$, and X is —$(CH_2)_n$—, these are preferably prepared with the process described, entirely by way of an example, for compounds ST1738 and ST1741, which involves a series of reactions according to the reaction diagram indicated here below:

It is understood that the expert in the field is capable of preparing all the formula (I) compounds, in which $R_1$ and $R_2$ are as specified in the general description, selecting the appropriate starting compounds. By way of an example, an appropriate starting compound will be selected from the group consisting of benzene 1,2-substituted with the groups $R_1$ and $R_2$ indicated above, such as 2-halophenol (2-chlorophenol, 2-fluorophenol, 2-bromophenol, 2-iodophenol), ethers with $C_1$–$C_4$ alkyl or $C_5$–$C_6$ cycloalkyl of 2-alkoxyphenol (2-chlorophenol methyl ether, 2-fluorophenol methyl ether, 2-bromophenol methyl ether, 2-iodophenol methyl ether and higher ethers). These compounds are commercially available or can be prepared with methods known in the literature.

In the case of the formula (I) compounds in which $R_3$ is —OH, the groups R1 and R2 are both alkoxy or cycloalkoxy, Y is —H, and X is —CO—$(CH_2)_n$—, these are preferably prepared with the process described, entirely by way of an example, for compound ST 1689, which involves a series of reactions according to diagram 2 here below.

Diagram 2

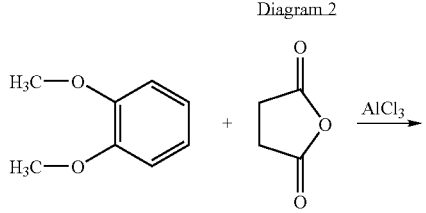

Diagram 3

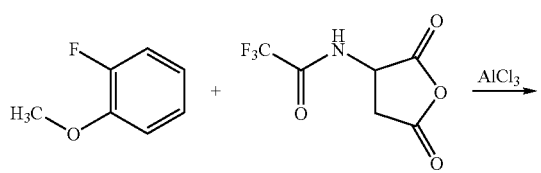

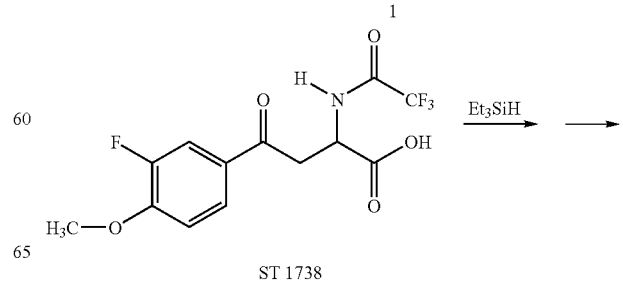

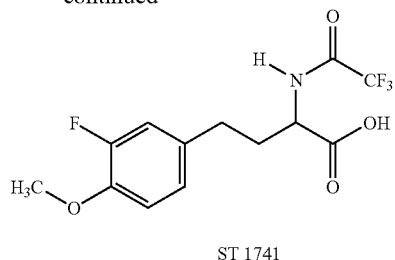

ST 1741

Of course, the chemical expert in the field will be capable of judging which procedural variants will enable him or her to obtain the compounds desired within the formula (I) framework described above, with the possible combinations envisaged for the various groups.

In particular, in the case of formula (I) compounds in which $R_3$ is $C_1$–$C_4$ alkoxy, $R_1$ and $R_2$ are alkoxy or cycloalkoxy, Y is —$CH_2COR_4$, and X is —$(CH_2)_n$— or X is —$CH_2$=, these are preferably prepared with the process described, entirely by way of an example, for compounds ST1503, ST1504, ST1505, ST1701 and ST1945, which involves a series of reactions according to the diagram indicated here below.

Of course, the chemical expert in the field will be capable of judging which procedural variants will enable him or her to obtain the compounds desired within the formula (I) framework described above, with the possible combinations envisaged for the various groups.

In particular, in the case of formula (I) compounds in which $R_3$ is $C_1$–$C_4$ alkoxy, $R_1$ and $R_2$ are alkoxy or cycloalkoxy, Y is —$(CH_2)COR_4$, and X is —$CH_2$=, these are preferably prepared with the process described, entirely by way of an example, for compound ST1977, which involves a series of reactions according to the diagram indicated here below.

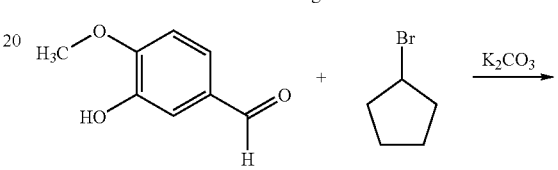

Diagram 5

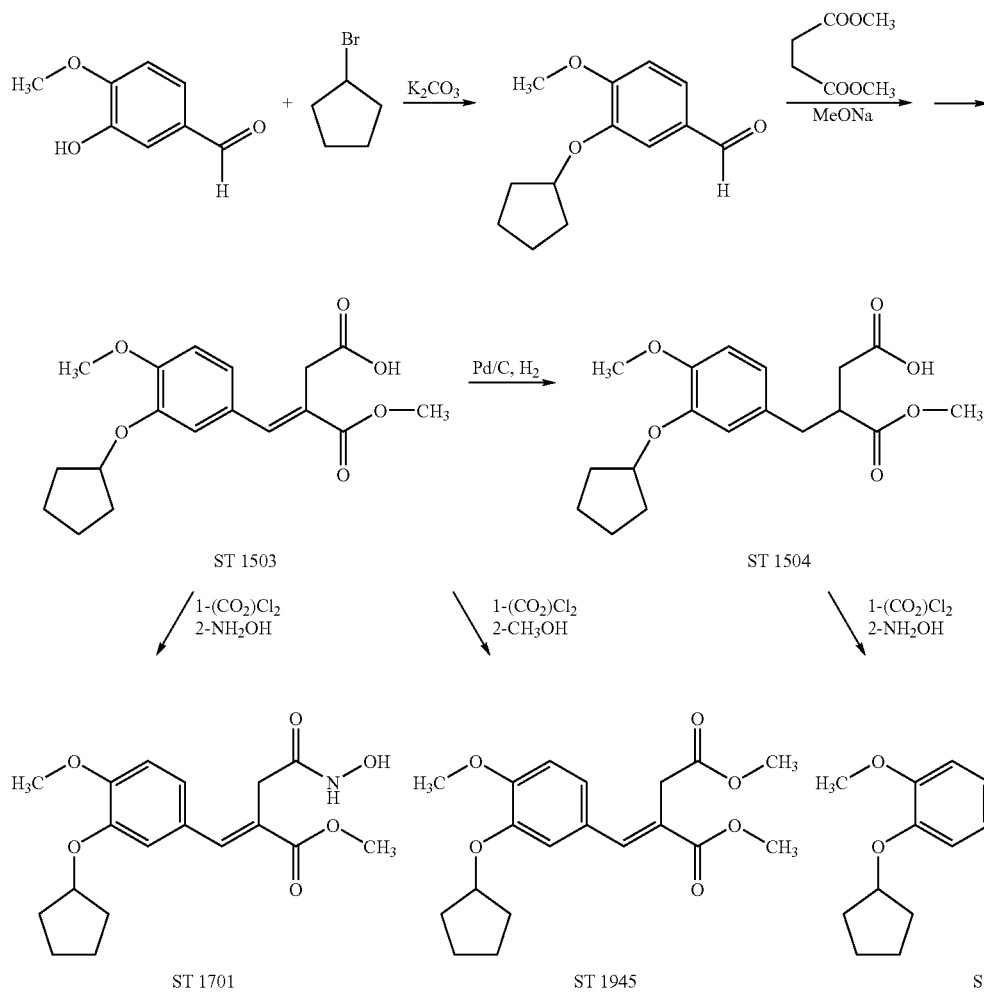

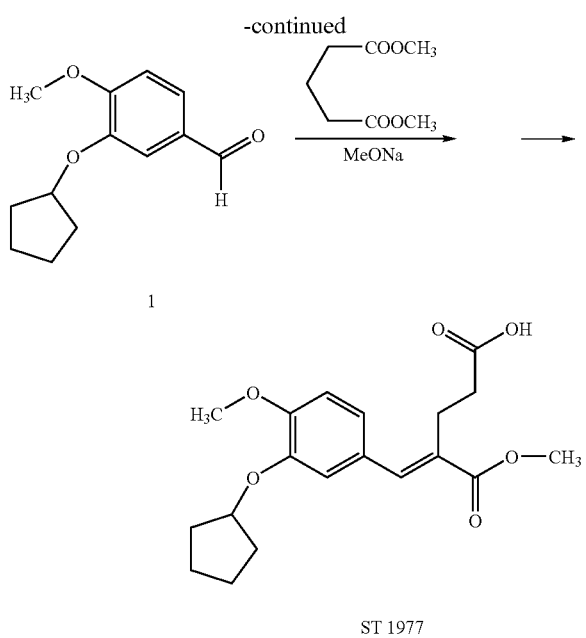

Of course, the chemical expert in the field will be capable of judging which procedural variants will enable him or her to obtain the compounds desired within the formula (I) framework described above, with the possible combinations envisaged for the various groups.

The following examples further illustrate the invention.

EXAMPLE 1 (DIAGRAM 1)

Preparation of (S)-4-(3-fluoro-4-methoxyphenyl)-2-amino-butanoic acid (ST1496)

Preparation of (S)-N-trifluoroacetyl-aspartic anhydride (1)

Aspartic acid (100 g: 0.75 mol) is suspended in trifluoroacetic acid (300 ml) under mechanical stirring and cooled with an ice and salt bath; trifluoroacetic anhydride is added drop-wise (300 ml: 2.16 mol), adjusting the addition in such a way as not to let the temperature rise above 10° C. On completing the addition, the suspension is left to stir vigorously for half an hour at a temperature below 10° C. after which the temperature is allowed to rise slowly. The suspension is reacted for 2 hours at 45° C. and for one night at room temperature. Extraction is done with acetone (300 ml) with cooling to solubilise the mass which is of very firm consistency and then the solution is concentrated to dryness. The solid obtained is washed twice with 500 cc of n-hexane and again with 1 liter of n-hexane/ethyl ether at a ratio of 4:1, triturating and vacuum filtering. 135 g of product are obtained which can be used as such if the analyses are compliant. Crystallisation by n-hexane/EtOAc is performed obtaining 119 g of product which is vacuum dried thoroughly at 40° C. Yield 75%.

M.P.: 116–118° C. $^1$H-NMR (CD$_3$OD) Varian 300 MHz, δ (ppm): 3.6 (2H,m,CH$_2$NH), 3.96 (3H,s,PhOCH$_3$); 4.88–5.01 (1H,m,CH$_2$CHNH); 7.18–7.22 (1H,t,Ar);7.7–7.8 (1H, dd, Ar); 7.82–7.9 (1h, bd, NH)

b) Preparation of (S)-4-(3-fluoro-4-methoxyphenyl-4-oxo-2-(N-trifluoroacetyl)aminobutanoic acid (ST1739)

The N-trifluoroacetyl aspartic anhydride (1) (58 g: 0.275 mol) is suspended in 100 ml of anhydrous CH$_2$Cl$_2$, 2-fluoroanisol (77 ml; 0.68 mol) is then added at room temperature and in a nitrogen atmosphere with mechanical stirring. The temperature is then brought down to +10° C. with an ice bath and AlCl$_3$ (82 g, 0.616 mol) is added in two portions. The cooling is removed and the suspension is left to reach room temperature. The reaction is left under mechanical stirring at room temperature for 2 days. After approximately 5 hours, when the reaction has taken on a red colour, and has started to become less fluid, another 100 ml of CH$_2$Cl$_2$ are added. When the reaction is completed, 300 ml of CH$_2$Cl$_2$ are added, the reaction mixture is left under vigorous stirring to triturate the solid and is then vacuum filtered. The dried solid is transferred portion-wise into a beaker containing 2 liters of HCl 6N under vigorous stirring and cooling with ice. A flaky precipitate is formed, the whole is extracted several times with a total of 1 liter of AcOEt or CH$_2$Cl$_2$, the organic phase is separated and brought to dryness after anhydrification on anhydrous Na$_2$SO$_4$. A clear solid or oil is obtained which is crystallised by n-hexane-EtOAc 7:5. Filtration is done by concentrating the mother waters from which further product is recovered which is recrystallised and added to the first crystallised product after TLC control. 43 g of product are obtained. Yield 47%.

M.P.: 116–118° C. $^1$H-NMR (CD$_3$OD) Varian 300 MHz, δ (ppm): 3.6 (2H,m,CH$_2$NH), 3,96 (3H,s,PhOCH$_3$); 4.88–5.01 (1H,m,CH$_2$CHNH); 7.18–7.22 (1H,t,Ar); 7.7–7.8 (1H, dd, Ar); 7.82–7.9 (1h, bd, NH)

Preparation of (S)-4-(3-fluoro-4-methoxyphenyl-2-(N-trifluoroacetyl)aminobutanoic acid (2)

(S)-4-(3-fluoro-4-methoxyphenyl-4-oxo-2-(N-trifluoroacetyl)

aminobutanoic acid (ST1738) (28.8 g, 0.087 mol) is dissolved in 150 ml of CF$_3$COOH or even less, and, under a nitrogen atmosphere, triethylsilane (54.9 g, 0.348 mol) is added; the solution is slightly refluxed for 8 hours and one night at room temperature. The trifluoroacetic acid is completely eliminated by vacuum evaporation at the lowest possible temperature; the residual oil is cooled with an ice and salt bath and then treated under stirring in a beaker with a saturated solution of NaHCO$_3$ and then with solid NaHCO$_3$, under vigorous stirring, adding ether from time to time to avoid excessive frothing. The aqueous phase is washed with ethyl ether and carefully acidified cold with HCl 6N to pH 3. The product precipitates and is then extracted several times with CH$_2$Cl$_2$. The organic extracts are gathered, washed with little water, dried on anhydrous Na$_2$SO$_4$ and then vacuum dried. The solid or oil obtained is crystallised by n-hexane/EtOAc obtaining a white solid which is vacuum dried in an oven. 21 g of product are obtained. Yield 75%.:

M.P.: 107–108° C. $^1$H-NMR (CDCl$_3$), Varian 300 MHz, δ(p.p.m.): 2.0–2.18 (1H,m,CHHCHNH); 2.22–2.36 (1H,m, CHHCHNH); 2.6–2.7 (2H,t,PhCH$_2$CH$_2$); 3.84 (3H,s, PhOCH$_3$); 4.6–4.7 (1H,m,CH$_2$CHNH), 6.78 (1H, dd, CHNHCOCF$_3$); 6.8–6.92 (2H,m,Ar).

d) Preparation of (S)-2-(N-trifluoroacetyl)amino-4-(3-fluoro-4-methoxyphenyl)butane-hydroxamic acid (ST 1471)

4.8 g (0.015 mol) of (S)-4-(3-fluoro-4-methoxyphenyl-2-(N-trifluoroacetyl)aminobutanoic acid (2) are suspended in 100 ml of anhydrous $CH_2Cl_2$; 1.15 ml of anhydrous DMF are added and after cooling at 0° C., 3 ml (0.035 mol) of oxalyl chloride are added drop-wise. The suspension is brought to room temperature and is reacted for 1 hour under stirring. The reaction mixture is cooled again to 0° C. and 25 ml of 50% $NH_2OH$ in water (0.374 mol) with 50 ml of THF are added drop-wise, leaving the solution to react at room temperature for another 2 hours. To the reaction mixture are added 200 ml of HCl 2N, extracting then several times with $CHCl_3$; the organic phase is then washed with water and concentrated to dryness, obtaining 3.9 g of crude product which, when crystallised several times by a mixture of solvents, gives 2.8 g of product. Yield 55%.

M.P.: 144–146° C. $^1$H-NMR ($CD_3OD$), Varian 300 MHz, δ(p.p.m.): 1.9–2.15 (2H,m,$CH_2$CHNH); 2.45–2.75 (2H,m,$CH_2$$CH_2$); 3.8 (3H,s,PhO$CH_3$); 4.1–4.2 (1H,t,$CH_2$$CH$NH), 4.5 (1H, m, $CH$NHCOCF$_3$); 6.8–7.1(3H,m,Ar).

e) Preparation of (S)-4-(3-fluoro-4-methoxyphenyl)-2-aminobutanoic acid (ST1496)

2.2 g (0.0068 mol) of (S)-2-(N-trifluoroacetyl)amino-4-(3-fluoro-4-methoxyphenyl)-butane-hydroxamic acid (ST 1471) are solubilised in 100 ml of anhydrous ethanol, and then, under a light nitrogen flow, 2.4 g of $NaBH_4$ are added by 0.8 g portions until the reaction is completed, leaving the solution to react for a total of 7 hours under stirring at room temperature. The solution is acidified with HCl 6N after cooling, the salts which have formed are filtered off and the aqueous solution is concentrated to eliminate ethanol, adding more water and washing with $CHCl_3$. The solution is then alkalinised cold to pH 8 with a saturated solution of $Na_2CO_3$, obtaining a solid which, when filtered and oven-dried, gives 1.1 g of product. Yield 68%.

M.P.: 164–167° C. $^1$H-NMR (DMSO$_{d6}$), Varian 200 MHz, δ (p.p.m.): 1.5–1.9 (2H,m,$CH_2$CHNH); 2.45–2.65 (2H,m,$CH_2$$CH_2$); 2.9–3.05 (1H,t,$CH_2$$CH$NH); 3.8 (3H,s, PhO$CH_3$); 6.9–7.1 (3H,m,Ar).

EXAMPLE 2 (DIAGRAM 2)

Preparation of 4-[3-(cyclopentyloxy)-4-Methoxyphenyl]-4-oxo-butanoic acid (ST 1689)

Preparation of 4-(3,4-dimethoxyphenyl)-4-oxo-butanoic acid (1)

11.4 g (0.09 mol) of 1,2-dimethoxybenzene are mixed with 3 g (0.03 mol) of succinic anhydride, and then, under stirring, the semisolid mass is added with 7.8 g (0.06 mol) of $AlCl_3$ under a light nitrogen flow. After 24 hours at room temperature under a nitrogen atmosphere, 300 ml of ethyl ether are added. A precipitate is formed which is filtered and treated by cooling with 100 ml of HCl 6N, extracting several times with $CH_2Cl_2$ and washing with water. The organic solution, anhydrified with anhydrous sodium sulphate, is concentrated to dryness, obtaining a yellow solid which is crystallised by n-hexane/EtOAc giving 3 g of product. Yield 50%.

M.P.: 160–162° C. $^1$H-NMR (CDCl$_3$), Varian 200 MHz, δ (p.p.m.): 2.7–2.8 (2H,m, $CH_2$); 3.2–3.4 (2H,m, $CH_2$); 3.93 (3H,s,PhO$CH_3$); 3.95 (3H,s,PhO$CH_3$); 6.8–6.95(1H,d,Ar); 7.5–7.6 (1H,s,Ar); 7.5–7.7 (1H,d,Ar).

Preparation of 4-[3-(cyclopentyloxy)-4-methoxyphenyl]-4-oxo-butanoic acid (ST 1689)

4.7 g (0.019 mol) of 4-(3,4-dimethoxyphenyl)-4-oxo-butanoic acid (FN 549) are dissolved in 50 ml of 47% HBr in water, heating to reflux for one hour until the reaction compound disappears. The reaction solution is concentrated to dryness, adding acetonitrile several times, and then the dark pitch is extracted hot several times with ethyl ether. On concentrating the organic solution to dryness, 3.3 g of crude product are obtained, which can be used as such in the next reaction. 3.3 g (0.015 mol) of crude 4-(3-hydroxy-4-methoxyphenyl)-4-oxo-butanoic acid (FN 551) are suspended in 30 ml of anhydrous DMF with 6.2 g (0.045 mol) of $K_2CO_3$, left under stirring for 30 minutes, and then added with 2.4 ml (0.0225 mol) of bromocyclopentane and heated at 70° C. for 4 hours under a nitrogen atmosphere. After one night at room temperature, the reaction mixture is dried under reduced pressure and the residue obtained is divided between HCl 2N and EtOAc, washing the organic phase with water. The reaction mixture is anhydrified on anhydrous sodium sulphate and evaporated to dryness, obtaining a dark oil which is chromatographed on a silica gel column, eluting with n-hexane/EtOAc. After crystallisation, the same mixture of solvents yields fractions containing the dried product. 0.63 g of product are obtained. Yield 14%.

M.P.: 111–113° C. $^1$H-NMR (DMSO$_{d6}$), Varian 300 MHz, δ(p.p.m.): 1.4–1.8 (8H,m,ciclopentile); 2.5–2.6 (2H,m, $CH_2$); 3.1–3.2 (2H,m, $CH_2$); 3.8 (3H,s,PhO$CH_3$); 4.9–5.1 (1H,t, $CH$); 7.0 (1H,d,Ar); 7.25 (1H,d,Ar); 7.45 (1H,d,Ar).

EXAMPLE 3 (DIAGRAM 3)

Preparation of 4-(3-fluoro-4-methoxyphenyl-4-oxo-2-(N-trifluoroacetyl)aminobutanoic acid (ST1738)

Preparation of N-trifluoroacetyl-aspartic anhydride (1)

Aspartic acid (100 g: 0.75 mol) is suspended in trifluoroacetic acid (300 ml) and cooled under mechanical agitation in an ice and salt bath; trifluoroacetic acid (300 ml: 2.16 mol) is added drop-wise, adjusting the addition so that the temperature does not rise above 10° C. On completing the addition, the suspension is left for half an hour under vigorous stirring at a temperature below 10° C., after which the temperature is allowed to rise slowly to room temperature. The solution is reacted for 2 hours at 45° C. and for 1 night at room temperature. Extraction is done with acetone (300 ml) and cooling to solubilise the mass which is of very firm consistency and the solution is then concentrated to dryness. The solid obtained is washed twice with 500 cc of n-hexane and then with 1 liter of n-hexane/ethyl ether at a ratio of 4:1, triturating and vacuum filtering. 135 g of product are obtained which can be used as such if the analyses are compliant. The product is crystallised by n-hexane/EtOAc obtaining 119 g of product which is vacuum dried thoroughly at 40° C. Yield 75%.

M.P.: 134–136° C. $^1$H-NMR (DMSO$_{d6}$), Varian 300 MHz, δ(p.p.m.): 2.85–3.3 (2H,m,$CH_2$); 4.95–5.1 (1H,m, CHNH); 9.6–9.8 (1H,bd,$CH$NHCOCF$_3$).

Preparation of 4-(3-fluoro-4-methoxyphenyl-4-oxo-2-(N-trifluoroacetyl)aminobutanoic acid (ST 1738)

N-trifluoroacetyl aspartic anhydride (1) (58 g: 0.275 mol) is suspended in 100 ml of anhydrous $CH_2Cl_2$, 2-fluoroanisol (77 ml; 0.68 mol) is then added at room temperature and in a nitrogen atmosphere with mechanical stirring. The temperature is then brought down to +10° C. with an ice bath and $AlCl_3$ (82 g: 0.616 mol) is added in two portions. The cooling is removed and the suspension is left to reach room temperature. The reaction is left under mechanical stirring at room temperature for 2 days. After approximately 5 hours, when the reaction has taken on a red colouring, and has started to become less fluid, another 100 ml of $CH_2Cl_2$ are added. When the reaction is complete, 300 ml of $CH_2Cl_2$ are added, the reaction mixture is left under vigorous stirring to triturate the solid and is then vacuum filtered. The dried solid is transferred portion-wise into a beaker containing 2 liters of HCl 6N under vigorous stirring and cooling with ice. A flaky precipitate is formed, the whole is extracted several times with a total of 1 liter of AcOEt or $CH_2Cl_2$, the organic phase is separated and brought to dryness after anhydrification on anhydrous $Na_2SO_4$. A clear solid or oil is obtained which is crystallised by n-hexane-EtOAc 7:5. Filtration is done by concentrating the mother waters from which another product is recovered which is recrystallised and added to the first crystallised product after TLC control. 43 g of product are obtained. Yield 47%.

M.P.: 116–118° C. $^1$H-NMR ($CD_3OD$) Varian 300 MHz, δ(ppm): 3.6 (2H,m,C$\underline{H}_2$CHNH), 3.96 (3H,s,PhOC$\underline{H}_3$); 4.88–5.01 (1H,m,CH$_2$C$\underline{H}$NH); 7.18–7.22 (1H,t,Ar); 7.7–7.8 (1H, dd, Ar); 7.82–7.9 (1H, bd, N$\underline{H}$).

EXAMPLE 4 (DIAGRAM 3)

Preparation of 4-(3-fluoro-4-methoxyphenyl-2-(N-trifluoroacetyl)aminobutanoic acid (ST1741)

(S)-4-(3-fluoro-4-methoxyphenyl-4-oxo-2-(N-trifluoroacetyl)
aminobutanoic acid (ST1738) (28.8 g 0.087 mol) is dissolved in 150 ml of $CF_3COOH$ or even less, and, under a nitrogen atmosphere, triethylsilane (54.9 g, 0.348 mol) is added; the solution is slightly refluxed for 8 hours and one night at room temperature. The trifluoroacetic acid is completely eliminated by vacuum evaporation at the lowest possible temperature; the residual oil is cooled with an ice and salt bath and then treated under stirring in a beaker with a saturated solution of $NaHCO_3$ and then with solid $NaHCO_3$, under vigorous stirring, adding ether from time to time to avoid excessive frothing. The aqueous phase is washed with ethyl ether and carefully acidified cold with HCl 6N to pH 3. The product precipitates and is then extracted several times with $CH_2Cl_2$. The organic extracts are united, washed with little water, dried on anhydrous $Na_2SO_4$ and then vacuum dried. The solid or oil obtained is crystallised by n-hexane/EtOAc obtaining a white solid which is vacuum dried in an oven. 21 g of product are obtained. Yield 75%.

M.P.: 107–108° C. $^1$H-NMR ($CDCl_3$), Varian 300 MHz, δ(p.p.m.): 2.0–2.18 (1H,m,CH$\underline{H}$CHNH); 2.22–2.36 (1H,m, CH$\underline{H}$CHNH); 2.6–2.7 (2H,t,PhC$\underline{H}_2$CH$_2$); 3.84 (3H,s, PhOC$\underline{H}_3$); 4.6–4.7 (1H,m,CH$_2$C$\underline{H}$NH), 6.78 (1H, dd, CHN$\underline{H}$COCF$_3$); 6.8–6.92 (2H,m,Ar).

EXAMPLE 5 (DIAGRAM 4)

Preparation of (3E)-4-[3-(cyclopentyloxy)-4-methoxyphenyl]-3-(methoxycarbonyl)-3-butenoic acid (ST1503)

To a solution of sodium methoxide in methanol, prepared by dissolving 4 g (0.174 mol) of sodium methylate in 100 ml of methanol, is added drop-wise, under a nitrogen atmosphere, a solution of 32.5 g (0.147 mol) of 3-cyclopentyloxy-4-methoxybenzaldehyde (1) and 19.8 ml (0.15 mol) of dimethyl succinate. The solution is then heated under stirring for 4 hours to reflux and, after cooling, is concentrated to dryness, obtaining an oily product, which after treatment with a saturated solution of $NaHCO_3$ at alkaline pH, is washed several times with ethyl ether. The aqueous solution is acidified with HCl 6N at pH 4 and the product is extracted several times with ethyl ether, washing with water until neutral pH is obtained. The organic phase is anhydrified with anhydrous sodium sulphate and concentrated to dryness. The crude solid obtained is crystallised by n-hexane/AcOEt, giving 20 g of product. Yield 41%.

M.P.:119–121° C. $^1$H-NMR ($CDCl_3$), Varian 300 MHz, δ(p.p.m.): 1.5–1.7 (2H,m,cyclopentyl); 1.7–2.0 (6H,m,cyclopentyl); 3.6 (2H,s,C$\underline{H}_2$COOH); 3.85 (3H,s,COOC$\underline{H}_3$); 3.87 (3H,s,OC$\underline{H}_3$); 4.75–4.82 (1H,m,OC$\underline{H}$); 6.85–7.0 (3H, m,Ar); 7.26 (1H,s,ArC$\underline{H}$=).

EXAMPLE 6 (DIAGRAM 4)

Preparation of 3-[3-(cyclopentyloxy-4-methoxybenzyl]-4-methoxy-4-oxobutanoic acid (ST 1504)

16.5 g (0.049 mol) of (3E)-4-[3-(cyclopentyloxy)-4-methoxyphenyl]-3-(methoxycarbonyl)-3-butenoic acid (ST1503) are solubilised in 450 ml of AcOEt, heating slightly; 1.8 g of Pd/C are added and the solution is hydrogenated in Parr at 52 p.s.i. for 3 hours. The suspension is filtered on a celite bed and concentrated to dryness, obtaining an oil, which solidifies after washing with petroleum ether. A crude product is obtained which when crystallised by n-hexane/AcOEt gives 12 g of product. Yield 73%.

P.F.: 68–70° C. $^1$H-NMR ($CDCl_3$), Varian 300 MHz, δ (p.p.m.): 1.5–1.7 (2H,m,cyclopentyl); 1.7–2.0 (6H,m,cyclopentyl); 2.38–2.5 (1H,m,C$\underline{H}_2$COOH); 2.6–2.8 (2H,m, C$\underline{H}_2$COOH,C$\underline{H}_2$Ar); 2.9–3.13 (2H,m,C$\underline{H}$COOCH$_3$, C$\underline{H}_2$Ar); 3.65 (3H,s,COOC$\underline{H}_3$); 3.8 (3H,s,OC$\underline{H}_3$); 4.68–4.8 (1H,m,OC$\underline{H}$); 6.6–6.82 (3H,m,Ar).

EXAMPLE 7 (DIAGRAM 4)

Preparation of (R,S)-3-methoxycarbonyl-4-(3-cyclopentyloxy-4-methoxyphenyl)butane-hydroxamic acid (ST 1505)

1.8 g (0.0053 mol) of ST1504 are solubilised in 40 ml of methylene chloride. 0.39 ml of N,N-DMF (0.00535 mol) are added under stirring at room temperature, the solution is cooled to 0° C. and 1.05 ml of oxalyl chloride is added (0.0123 mol). The solution is maintained for 1 hour at room temperature and then cooled again to 0° C. and 8.14 ml (0.133 mol) of 50% hydroxylamine in $H_2O$ is added drop-wise, diluted with 16 ml of THF. The solution is held for 2 hours at room temperature under stirring, acidified cold with HCl 2N 50 ml and the solution is extracted twice with CHCl$_3$. The CHCl$_3$ washed with H$_2$O until neutral pH is achieved, is dried on anhydrous sodium sulphate and vacuum concentrated. 1.9 g of oily product are obtained which is crystallised by a mixture of ethyl ether 20 ml and AcOEt 5 ml—hexane 10 ml.

M.P.: 114°–117° C.

EXAMPLE 8 (DIAGRAM 4)

Preparation of methyl (2E)-3-[3-(cyclopentyloxy)-4-methoxyphenyl]-2-[2-(hydroxyamino)-2-oxoethyl]-2-propenoate (ST1701)

1,4 g (0.0042 mol) of ST 1503 are solubilised in 3,5 ml of methylene chloride. 0.31 ml of N,N-DMF (0.0042 mol), are added under stirring at room temperature, the solution is cooled to 0° C. and 0.85 ml (0.0097 mol) of oxalyl chloride is added.

The solution is maintained for 1 hour at room temperature and then cooled again to 0° C. and 7 ml (0.105 mol) of 50% hydroxylamine in H$_2$O is added drop-wise, diluted with 14 ml of THF.

The solution is held for 2 hours at room temperature under stirring, acidified cold with HCl 2N 55 ml and the solution is extracted twice with CHCl$_3$. The CHCl$_3$ washed with H$_2$O until neutral pH is achieved, is dried on anhydrous sodium sulphate and vacuum concentrated. 1 g of oily yellow product are obtained which is crystallised by a mixture of isopropyl ether and AcOEt. Yield 68%.

M.P. 142–144° C. $^1$H-NMR (CDCl$_3$), Varian 300 MHz, δ (p.p.m.): 1.5–2.1 (8H,m,ciclopentyl); 3.45 (2H,s,CH$_2$); 3.85 (3H,s,COOCH$_3$); 3.9 (3H,s,OCH$_3$); 4.95 (1H,m,CH); 6.9–7.2 (2H,dd,Ar); 7.45 (1H,s,Ar); 7.82 (1H,s,Ph—CH=); 7.6–7.9 (1H,bs,OH); 9.2 (1H,bs,NH).

EXAMPLE 9 (DIAGRAM 4)

Preparation of methyl (3E)-3-methoxycarbonyl-4-(3-cyclopentoxy-4-methoxyphenyl)-3-butenoate (ST 1945)

1.67 g (0.005 mol) of (3E)-4-[3-(cyclopentyloxy)-4-methoxyphenyl]-3-(methoxycarbonyl)-3-butenoic acid are suspended in 8 ml of methylene chloride. 0.36 ml of N,N-DMF (0.005 mol), are added under stirring at room temperature, the solution is cooled to 0° C. and 0.87 ml (0.01 mol) of oxalyl chloride is added.

The solution is maintained for 1 hour at room temperature and then the solvent is completely eliminated by vacuum evaporation. To the amorphous coloured solid obtained 6 ml of methanol is added at 0° C.

The solution is held for 2 hours at room temperature under stirring, the solvent is completely eliminated by vacuum evaporation. 1.2 g of a dark oily product obtained is purified by flash-chromatography on silica gel, eluting with n-hexane/EtOAc 8:2. 600 mg of crystallised product is obtained from the fractions when the solvent is eliminated by vacuum evaporation. Yield 34%.

$^1$H-NMR (CDCl3), Varian 300 MHz, δ (p.p.m.): 1.5–1.7 (2H,m,ciclopentyl); 1.7–2.0 (6H,m,ciclopentyl); 3.58 (2H,s, CH$_2$COOH); 3.75 (3H,s,CH$_2$COOCH$_3$); 3.83 (3H,s, COOCH$_3$); 3.87 (3H,s,OCH$_3$); 4.7–4.8 (1H,m,OCH); 6.85–7.0 (3H,m,Ar); 7.83 (1H,s,ArCH=).

EXAMPLE 10 (DIAGRAM 5)

Preparation of (4E)-5-[3-(ciclopentyloxy)-4-methoxyphenyl]-4-(methoxycarbonyl)-4-pentenoic acid (ST 1977)

To a solution of sodium methoxide in methanol, prepared by dissolving 0.26 g (0.011 mol) of sodium methylate in 8 ml of methanol, is added drop-wise, under a nitrogen atmosphere, a solution of 2.0 g (0.00908 mol) of 3-cyclopentyloxy-4-methoxybenzaldehyde (1) and 1.5 ml (0.01 mol) of dimethyl glutarate.

The solution is then heated under stirring for 2.5 hours to reflux and, after cooling, is concentrated to dryness, obtaining an oily product, which after treatment with a solution of NaHCO$_3$ at alkaline pH, is washed several times with ethyl ether.

The aqueous solution is acidified with HCl 6N at pH 3 and the product is extracted several times with ethyl ether, washing with water until neutral pH is obtained. The organic phase is anhydrified with anhydrous sodium sulphate and concentrated to dryness. The crude solid obtained is crystallised by n-hexane/AcOEt, giving 0.4 g of product. Yield 13%.

M.P.: 99–101° C. $^1$H-NMR (CDCl$_3$), Varian 300 MHz, δ (p.p.m.): 1.5–1.7 (2H,m,ciclopentyl); 1.7–2.0 (6H,m,ciclopentyl); 2.62 (2H,t,CH$_2$COOH); 2.95 (2H,t,CH$_2$CH$_2$COOH) 3.85 (3H,s,COOCH$_3$); 3.87 (3H,s,OCH$_3$); 4.75–4.82 (1H,m,OCH); 6.85–7.0 (3H,m,Ar); 7.65 (1H,s, ArCH=).

The compounds according to the invention described herein are useful as PDE IV inhibitors.

Assays conducted with standard procedures, e.g. as described by Cortij et al., Br. J. Pharmacol. 108:562, 1993 or Nicholsen CD et al., Trends Pharmacol. Sci. 12:19, 1991 have yielded the following results for compounds figuring among the examples envisaged within the framework of the invention described herein.

| Compound | Species | Concentration (μM) | % inhibition |
|---|---|---|---|
| ST 1504 | human | 100 | 84 |
| ST 1505 | human | 100 | 86 |
| ST 1701 | human | 100 | 88 |

The following determination of IC$_{50}$ for inhibition of PDE IV activity and competition at the rolipram receptor, conducted with standard processes, e.g. as described by Duplantier A. J. et al., J. Med. Chem. 39: 120, 1996 and by Thorphy T. J. et al., J Pharmacol. Exp. Ther., 263: 1195, 1992 have yielded the following results for compounds figuring among the examples envisaged within the framework of the invention described herein

| Compound | Origin | IC$_{50}$(μM) PDE4 Activity (L)PDE4 | Origin | IC$_{50}$(μM) Rolipram receptor (H)PDE4 | H/L |
|---|---|---|---|---|---|
| ST 1945 | Human | 0.19 | Mouse brain | 0.571 | 0.33 |
| ST 1701 | Human | 1.2 | Mouse brain | 0.615 | 0.51 |

-continued

| Compound | Origin | IC$_{50}$(μM) PDE4 Activity (L)PDE4 | Origin | IC$_{50}$(μM) Rolipram receptor (H)PDE4 | H/L |
|---|---|---|---|---|---|
| ST 1977 | Human | 1.3 | Mouse brain | 9.27 | 7.13 |
| ST 1505 | Human | 4.7 | Mouse brain | 3.5 | 0.74 |
| ST 1503 | Human | 6.2 | Mouse brain | N.C. | — |
| ST 1504 | Human | 8.7 | Mouse brain | >10.0 | >1.15 |

N.C. means value not calculable because of no inhibition at the highest test concentration, however it means low affinity for rolipram receptor.

As reported in WO 00/51598, authors: Christensen S. B., Barnette M. S. and Thorphy T. J. and widely confirmed by other authors in related literature, if a compound exhibits H/L IC$_{50}$ ratio of about 0.1 or greater calculated as the ratio of the IC$_{50}$ (H) for high affinity rolipram binding form (HPDE4) divided by the IC$_{50}$ (L) for the form which binds rolipram with low affinity (LPDE4), it will have an acceptable therapeutic index for treating asthma or chronic obstructive pulmonary disease (COPD), minimising side effects typical of phosphodiesterase IV inhibitors as rolipram.

Selectivity of these compounds for inhibition of phosphodiesterase IV (PDE4) activity over other phosphodiesterases was demonstrated by assays conducted with standard processes, e.g. as described by Nicholsen CD et al., Trends Pharmacol. Sci. 12:19, 1991. These assays have yielded the following results for compounds figuring among the examples envisaged within the framework of the invention described herein.

| | % PDE inhibition at 100 μM | | | | | |
|---|---|---|---|---|---|---|
| Compound | PDE1 (bovine) | PDE2 (human) | PDE3 (human) | PDE4 (human) | PDE5 (human) | PDE6 (bovine) |
| ST 1701 | 42 | 16 | 52 | 94 | 30 | 58 |

The compounds according to the invention described herein are useful as medicaments, and particularly as phosphodiesterase IV inhibitors. The compounds according to the invention can therefore be used in the preparation of medicaments with phosphodiesterase IV inhibitory activity, particularly for the treatment of asthma or for the treatment of chronic obstructive pulmonary disease.

The compounds according to the invention also exert an inhibitory action on the release of TNF (Tumor Necrosis Factor) induced by bacterial LPS (lipopolysaccharides). In in-vitro activity tests, conducted as described in the International patent application WO 98/33762, the compounds according to the invention have demonstrated a TNF inhibitory action comparable to that shown by the compounds described in 98/33762.

Therefore, the compounds according to the invention are useful as medicaments, particularly for the treatment and prevention of septic shock.

As far as industrial applicability is concerned, the formula (I) compounds described herein will be formulated in pharmaceutical compositions as active ingredients. Pharmaceutical compositions are conventionally known and contain a therapeutically effective amount of active ingredient in mixtures with pharmaceutically acceptable excipients and/or vehicles.

The subject matter of the invention described herein comprises pharmaceutical compositions containing as their active ingredient at least one formula (I) compound, either alone or in combination with one or more formula (I) compounds. The active ingredient according to the invention described herein will be in admixture with appropriate vehicles and/or excipients commonly used in pharmaceutical technology, such as, for example, those described in "Remington's Pharmaceutical Sciences Handbook", latest edition. The compositions according to the invention described herein will contain a therapeutically effective amount of the active ingredient. The doses will be decided by the expert in the field, e.g. by the clinician or primary care physician according to the type of disease to be treated and the patient's condition, or concomitantly with the administration of other active ingredients. By way of an example, doses ranging from 0.1 to 100 mg/kg may be indicated.

Examples of pharmaceutical compositions are those that permit oral or parenteral, intravenous, intramuscular, subcutaneous, and transdermal administration as well as administration by nasal or oral spray. Pharmaceutical compositions suitable for the purpose are tablets, soft or rigid capsules, powders, solutions, suspensions, syrups, and solid forms for extemporary liquid preparations. Compositions for parenteral administration include, for example, all the intramuscular, intravenous and subcutaneous injectable forms and those which can be administered in the form of solutions, suspensions, or emulsions. We should also mention the liposomal formulations. The compositions also include forms entailing the controlled release of the active ingredient, whether in oral administration, as tablets coated with various layers, microencapsulated powders, complexes with cyclodextrin, and depot forms, e.g. of the subcutaneous type, or as depot injections and implants.

What is claimed is:
1. A compound selected from the group consisting of:
(S)-2-(N-trifluoroacetyl)amino-4-(3-fluoro-4-methoxyphenyl)-butane-hydroxamic acid);
(S)-2-amino-4-(3-fluoro-4-methoxyphenyl)-butane-hydroxamic acid;
(3E)-3-methoxycarbonyl-4-(3-cyclopentoxy-4-methoxyphenyl)-3-butenoic acid;
(R,S)-3-methoxycarbonyl-4-(3-cyclopentoxy-4-methoxyphenyl)-butanoic acid;
4-oxo-4-(3-cycopentyloxy-4-methoxyphenyl)-butanoic acid;
methyl (2E)-3-[3-(cyclopentyloxy)-4-methoxyphenyl]-2-[2-(hydroxyamino)-2-oxoethyl]-2-propenoate;
4-(3-fluoro-4-methoxyphenyl)-4-oxo-2-[(trifluoroacetyl)-amino]-butanoic acid;
(2S)-4-(3-fluoro-4-methoxyphenyl)-4-oxo-2-[(trifluoroacetyl) amino]butanoic acid;
4-(3-fluoro-4-methoxyphenyl)-2-[(trifluoroacetyl) amino]-butanoic acid;
(R,S)-3-methoxycarbonyl-4-(3-cyclopentyloxy-methoxyphenyl)butane-hydroxamic acid;
methyl (3E)-3-methoxycarbonyl-4-(3-cyclopentoxy-4-methoxyphenyl)-3-butenoate; and
(4E)-5-[3-(ciclopentyloxy)-4-methoxyphenyl]-4-(methoxycarbonyl)-4-pentenoic acid.

2. A pharmaceutical composition containing at least one compound of Formula (I):

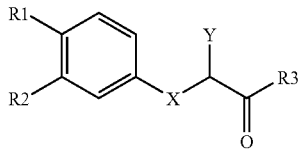

where:
R$_1$ and R$_2$, which may be the same or different, are halogen, hydroxy, straight or branched C$_1$–C$_4$ alkoxy, or C$_5$–C$_6$ cycloalkoxy provided that at one of the R$_1$ or R$_2$ is C$_5$–C$_6$ cycloalkoxy;
X is —(CH$_2$)$_n$—, —CO—(CH$_2$)$_n$—, where n is 1 or 2 or K is —CH═;
R$_3$ is OH, —NHOH, straight or branched C$_1$–C$_4$ alkoxy;
Y is H, —(CH$_2$)$_n$COR$_4$, —COR$_4$, —NHR$_5$, where R$_4$ is OH, —NHOH, straight or branched C$_1$–C$_4$ alkoxy, R$_5$ is H, C$_1$–C$_4$ alkanoyl optionally substituted by halogens;
and n is an integer of 1 to 4;
provided that the compound is not 3-(3-cyclopentyloxy-4-methoxybenzyl)-n-propanoic acid or 3-(3-cyclopentyloxy-4-methoxybenzyl)-E-propenoic acid;
its enantiomer, diastereoisomer and mixtures of the same, and its pharmaceutically acceptable salt in admixture with at least one pharmaceutically acceptable vehicle or excipient.

3. A compound of Formula (I):

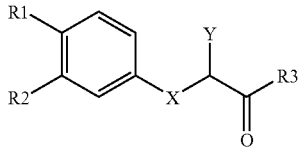

where: R$_1$ and R$_2$, which may be the same or different, are halogen, hydroxy, straight or branched C$_1$–C$_4$ alkoxy, or C$_5$–C$_6$ cycloalkoxy, provided that at least one of R$_1$ or R$_2$ is C$_5$–C$_6$ cycloalkoxy;
X is —(CH$_2$)$_n$—, —CO—(CH$_2$)$_n$—, where n is 1 or 2, or X is —CH═;
R$_3$ is OH, —NHOH, straight or branched C$_1$–C$_4$ alkoxy;
Y is H, —(CH$_2$)$_n$COR$_4$, —COR$_4$, —NHR$_5$, where R$_4$ is OH, —NHOH, straight or branched C$_1$–C$_4$ alkoxy, R$_5$ is H, C$_1$–C$_4$ alkanoyl optionally substituted by halogens;
and n is an integer of 1 to 4;
provided that the compound is not 3-(3-cyclopentyloxy-4-methoxybenzyl)-n-propanoic acid or 3-(3-cyclopentyloxy-4-methoxybenzyl)-E-propenoic acid
and provided that the compound is not 3-cyclopentlyoxy-4-methoxybenzyl idenemalonic acid diethyl ester;
its enantiomer, diastereoisomer and mixtures of the same, and its pharmaceutically acceptable salt.

4. The compound according to claim 3, in which R$_1$ is halogen and R$_2$ cycloalkoxy.

5. The compound according to claim 3, in which R$_3$ is —NHOH.

6. The compound according to claim 3, in which X is —CH═.

7. The compound according to claim 3, in which R$_3$ is OH.

8. The compound according to claim 3, in which Y is —(CH$_2$)$_n$COR$_4$, where R$_4$ is —NHOH.

9. The compound according to claim 3, in which Y is —(CH$_2$)$_n$COR$_4$, where n is 2 and R$_4$ is OH.

10. The compound according to claim 3, in which Y is —(CH$_2$)$_n$COR$_4$, where n is 1 and R$_4$ is straight or branched C$_1$–C$_4$ alkoxy.

11. A method of treating asthma comprising administering to a subject in need thereof an effective amount of a compound of the formula:

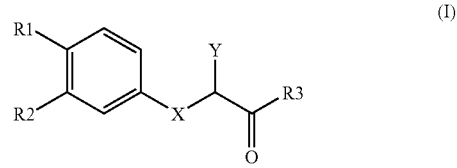

where:
R$_1$ and R$_2$, which may be the same or different, are halogen, hydroxy, straight or branched C$_1$–C$_4$ alkoxy, C$_5$–C$_6$ cycloalkoxy;
X is —(CH$_2$)$_n$—, —CO—(CH$_2$)$_n$—, where n is 1 or 2, or X is —CH═;
R$_3$ is OH, —NHOH, straight or branched C$_1$–C$_4$ alkoxy;
Y is H, —(CH$_2$)$_n$COR$_4$, —COR$_4$, —NHR$_5$, where R$_4$ is OH, —NHOH, straight or branched C$_1$–C$_4$ alkoxy, R$_5$ is H, C$_1$–C$_4$ alkanoyl optionally substituted by halogens;
n is an integer of 1 to 4;
provided that the compound is not 3-(3-cycopentyloxy-4-methoxybenzyl)-n-propanoic acid or 3-(3-cyclopentyloxy-4-methoxybenzyl)-E-propenoic acid
and provided that the compound is not 3-cyclopentlyoxy-4-methoxybenzyl idenemalonic acid diethyl ester;
its enantiomer, diastereoisomer and mixtures of the same, and its pharmaceutically acceptable salt.

12. A method of treating a chronic obstructive pulmonary disease comprising administering to a subject in need thereof an effective amount of a compound of the formula:

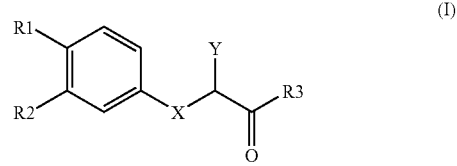

where:
R$_1$ and R$_2$, which may be the same or different, are halogen, hydroxy, straight or branched C$_1$–C$_4$ alkoxy, C$_5$–C$_6$ cycloalkoxy;
X is —(CH$_2$)$_n$—, —CO—(CH$_2$)$_n$—, where n is 1 or 2, or X is —CH═;
R$_3$ is OH, —NHOH, straight or branched C$_1$–C$_4$ alkoxy;
Y is H, —(CH$_2$)$_n$COR$_4$, —COR$_4$, —NHR$_5$, where R$_4$ is OH, —NHOH, straight or branched C$_1$–C$_4$ alkoxy, R$_5$ is H, C$_1$–C$_4$ alkanoyl optionally substituted by halogens;
n is an integer of 1 to 4;
provided that the compound is not 3-(3-cyclopentyloxy-4-methoxybenzyl)-n-propanoic acid or 3-(3-cyclopentyloxy-4-methoxybenzyl)-E-propenoic acid and provided that the compound is not 3-cyclopentlyoxy-4-methoxybenzyl idenemalonic acid diethyl ester;

its enantiomer, diastereoisomer and mixtures of the same, and its pharmaceutically acceptable salt.

13. A method of treating septic shock comprising administering to a subject in need thereof an effective amount of a compound of the formula:

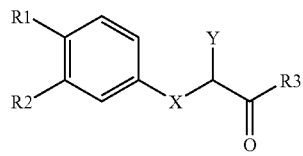
(I)

where:

$R_1$ and $R_2$, which may be the same or different, are halogen, hydroxy, straight or branched $C_1$–$C_4$ alkoxy, $C_5$–$C_6$ cycloalkoxy;

X is —$(CH_2)_n$—, —CO—$(CH_2)_n$—, where n is 1 or 2, or X is —CH=;

$R_3$ is OH, —NHOH, straight or branched $C_1$–$C_4$ alkoxy;

Y is H, —$(CH_2)COR_4$, —$COR_4$, —$NHR_5$, where $R_4$ is OH, —NHOH, straight or branched $C_1$–$C_4$ alkoxy, $R_5$ is H, $C_1$–$C_4$ alkanoyl optionally substituted by halogens;

n is an integer of 1 to 4;

its enantiomer, diastercoisomer and mixtures of the same, and its pharmaceutically acceptable salt.

* * * * *

UNITED STATES PATENT AND TRADEMARK OFFICE
CERTIFICATE OF CORRECTION

PATENT NO. : 7,169,808 B2
APPLICATION NO. : 10/311756
DATED : January 30, 2007
INVENTOR(S) : Fanto' et al.

It is certified that error appears in the above-identified patent and that said Letters Patent is hereby corrected as shown below:

Claim 1
Col. 16 Line 40-67
1. A compound selected from the group consisting of:
- (S)-2-(N-trifluoroacetyl)amino-4-(3-fluoro-4-methoxyphenyl)-butane-hydroxamic acid);
- (S)-2-amino-4-(3-fluoro-4-methoxyphenyl)-butane-hydroxamic acid;
- (3E)-3-methoxycarbonyl-4-(3 -cyclopentoxy-4-methoxyphenyl)-3-butenoic acid;
- (R, S)-3-methoxycarbonyl-4-(3-cyclopentoxy-4-methoxyphenyl)-butanoic acid;
- 4-oxo-4-(3-cyclopentyloxy-4-methoxyphenyl)-butanoic acid;
- methyl (2E)-3-[3-(cyclopentyloxy)-4-methoxyphenyl]-2-[2-(hydroxyamino)-2-oxoethyl]-2-propenoate;
- 4-(3-fluoro-4-methoxyphenyl)-4-oxo-2-[(trifluoroacetyl)-amino]-butanoic acid;
- (2S)-4-(3-fluoro-4-methoxyphenyl)-4-oxo-2-[(trifluoro-acetyl) amino]butanoic acid;
- 4-(3-fluoro-4-methoxyphenyl)-2-[(trifluoroacetyl)amino]-butanoic acid;
- (R, S)-3-methoxycarbonyl-4-(3-cyclopentyloxy-methoxyphenyl)butane-hydroxamic acid;
- methyl (3E)-3-methoxycarbonyl-4-(3-cyclopentyloxy-4-methoxyphenyl)-3-butenoate; and
- (4E)-5-[3-(ciclopentyloxy)-4-methoxyphenyl]-4-(methoxycarbonyl)-4-pentenoic acid.

Claim 2 Col. 17 Line 1-32
2. A pharmaceutical composition containing at least one compound of Formula (I):

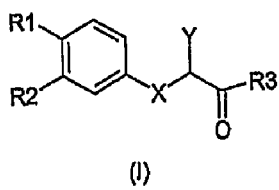

(I)

where:
$R_1$ and $R_2$, which may be the same or different, are halogen, hydroxy, straight or branched $C_1$-$C_4$ alkoxy, or $C_5$-$C_6$ cycloalkoxy provided that at one of the $R_1$ or $R_2$ is $C_5$-$C_6$ cycloalkoxy;
X is -$(CH_2)_n$-, -CO-$(CH_2)_n$-, where n is 1 or 2, or X is –CH=;
$R_3$ is OH, -NHOH, straight or branched $C_1$-$C_4$ alkoxy;
Y is H, -$(CH_2)_n COR_4$, -$COR_4$, -$NHR_5$, where $R_4$ is OH, -NHOH, straight or branched $C_1$-$C_4$ alkoxy, $R_5$ is H, $C_1$-$C_4$ alkanoyl optionally substituted by halogens;

UNITED STATES PATENT AND TRADEMARK OFFICE
CERTIFICATE OF CORRECTION

PATENT NO. : 7,169,808 B2
APPLICATION NO. : 10/311756
DATED : January 30, 2007
INVENTOR(S) : Fanto' et al.

It is certified that error appears in the above-identified patent and that said Letters Patent is hereby corrected as shown below:

and n is an integer of 1 to 4;
    provided that the compound is not 3-(3-cyclopentyloxy-4-methoxybenzyl)-n-propanoic acid or 3-(3-cyclopentyloxy-4-methoxybenzyl)-E-propenoic acid;
    its enantiomer, diastereoisomer and mixtures of the same, and its pharmaceutically acceptable salt in admixture with at least one pharmaceutically acceptable vehicle or excipient.

Signed and Sealed this

Thirty-first Day of July, 2007

JON W. DUDAS
*Director of the United States Patent and Trademark Office*